(12) United States Patent
Schwab

(10) Patent No.: US 12,310,629 B2
(45) Date of Patent: May 27, 2025

(54) METHODS AND DEVICES FOR AUGMENTING THE SPINE

(71) Applicant: Frank J. Schwab, New York, NY (US)

(72) Inventor: Frank J. Schwab, New York, NY (US)

(73) Assignee: Alphatec Spine, Inc., Carlsbad, CA (US)

( * ) Notice: Subject to any disclaimer, the term of this patent is extended or adjusted under 35 U.S.C. 154(b) by 0 days.

(21) Appl. No.: 17/172,306

(22) Filed: Feb. 10, 2021

(65) Prior Publication Data
US 2022/0249133 A1 Aug. 11, 2022

(51) Int. Cl.
*A61B 17/70* (2006.01)

(52) U.S. Cl.
CPC ...... *A61B 17/7022* (2013.01); *A61B 17/7053* (2013.01); *A61B 17/707* (2013.01)

(58) Field of Classification Search
CPC ............ A61B 17/7022; A61B 17/7026; A61B 17/7029; A61B 17/7031; A61B 17/7067
See application file for complete search history.

(56) References Cited

U.S. PATENT DOCUMENTS

| | | | |
|---|---|---|---|
| 5,092,889 A | 3/1992 | Campbell, Jr. | |
| 5,562,660 A | 10/1996 | Grob | |
| 6,290,700 B1 | 9/2001 | Schmotzer | |
| 6,296,643 B1 | 10/2001 | Hopf et al. | |
| 6,645,211 B2 | 11/2003 | Magana | |
| 8,162,993 B2 | 4/2012 | Ferree | |
| 8,454,662 B2 | 6/2013 | Bethell | |
| 8,470,002 B2 | 6/2013 | Allard et al. | |
| 9,220,536 B2 | 12/2015 | Skaggs | |
| 9,770,266 B2 | 9/2017 | Hestad | |
| 9,844,397 B2 | 12/2017 | Carls | |
| 9,949,761 B2 | 4/2018 | Fening et al. | |
| 2005/0177164 A1 | 8/2005 | Walters et al. | |
| 2005/0261695 A1 | 11/2005 | Cragg et al. | |
| 2005/0277919 A1 | 12/2005 | Slivka et al. | |
| 2006/0009846 A1 | 1/2006 | Trieu et al. | |
| 2006/0089646 A1* | 4/2006 | Bonutti | A61L 27/3834 606/279 |
| 2006/0149237 A1 | 7/2006 | Markworth et al. | |
| 2006/0276788 A1 | 12/2006 | Berry et al. | |
| 2006/0276895 A1 | 12/2006 | Pellegrino et al. | |
| 2007/0005137 A1 | 1/2007 | Kwak | |
| 2007/0129729 A1 | 6/2007 | Petit et al. | |

(Continued)

FOREIGN PATENT DOCUMENTS

| | | | |
|---|---|---|---|
| EP | 2138122 A1 * | 12/2009 | ......... A61B 17/7022 |
| WO | WO2017201437 | 11/2017 | |

OTHER PUBLICATIONS

International Search Report and Written Opinion dated Apr. 14, 2020 in related International Application No. PCT/US19/66027 filed Dec. 12, 2019 (9 pages).

(Continued)

*Primary Examiner* — Julianna N Harvey
(74) *Attorney, Agent, or Firm* — Dentons US LLP

(57) ABSTRACT

The present disclosure provides a device to restrict interspinous motion across multiple segments of a spinal column in a patient, comprising at least a first ligamentous line attached to a spinous process, a soft tissue in proximity to posterior aspects of a spinal vertebrae, or a pre-existing spinal fixation device or system.

34 Claims, 9 Drawing Sheets

(56) References Cited

U.S. PATENT DOCUMENTS

| | | |
|---|---|---|
| 2007/0288011 A1 | 12/2007 | Logan |
| 2007/0288024 A1 | 12/2007 | Gollogly |
| 2008/0009866 A1* | 1/2008 | Alamin ............. A61B 17/7053 606/151 |
| 2008/0033436 A1 | 2/2008 | Song et al. |
| 2008/0140123 A1 | 6/2008 | Ferree |
| 2008/0234737 A1 | 9/2008 | Boschert |
| 2008/0255615 A1 | 10/2008 | Vittur et al. |
| 2009/0281573 A1* | 11/2009 | Biedermann ...... A61B 17/7029 606/264 |
| 2009/0281574 A1 | 11/2009 | Jackson |
| 2010/0094302 A1 | 4/2010 | Pool et al. |
| 2010/0174319 A1 | 7/2010 | Jackson |
| 2010/0217271 A1 | 8/2010 | Pool et al. |
| 2012/0035661 A1 | 2/2012 | Pool et al. |
| 2012/0071928 A1 | 3/2012 | Jackson |
| 2012/0143255 A1 | 6/2012 | Jackson et al. |
| 2013/0035726 A1 | 2/2013 | Nguyen et al. |
| 2014/0025166 A1 | 1/2014 | Bonutti |
| 2014/0094854 A1 | 4/2014 | Schwab |
| 2014/0358150 A1 | 12/2014 | Kaufman et al. |
| 2016/0000468 A1 | 1/2016 | Samdani et al. |
| 2016/0346010 A1 | 12/2016 | Jackson |
| 2017/0231661 A1 | 8/2017 | Bannigan et al. |
| 2018/0140327 A1 | 5/2018 | Yue |
| 2018/0353216 A1 | 12/2018 | Mundis, Jr. |
| 2019/0167314 A1 | 6/2019 | Mosnier |
| 2020/0187993 A1* | 6/2020 | Schwab ............. A61B 17/7091 |

OTHER PUBLICATIONS

Lowe et al., A posterior tether for fusionless modulation of sagittal plane growth in a sheep model, Spine (Phila Pa 1976). Sep. 1, 2005;30(17 Suppl):S69-74.

Skaggs et al., Improvement of Kyphoscoliosis in a 9-Year-Old Using Growth Modulation With a Posterior Tether: A Case Report, Spine Deform. Jan. 2013;1(1):79-83. doi: 10.1016/j.jspd.2012.09.002. Epub Jan. 3, 2013.

Zimmer, Dynesys Top-Loading System Surgical Technique, The Dynamic Stabilization System, https:/www.zimmerbiomet.com/content/dam/zimmer-biomet/medical-professionals/000-surgical-techniques/spine/dynesys-top-loading-system-surgical-technique.pdf, downloaded from internet Dec. 2019 (44 pages).

Zimmer, The Tether—Vertebral Body Tethering System, https://www.ida.gov/medical-devices/recently-approved-devices/tethertm-vertebral-body-tethering-system-h190005, downloaded from internet Dec. 2019 (3 pages).

International Search Report and Written Opinion dated May 16, 2022 in related International Application No. PCT/US2022/016026 filed Feb. 10, 2022 (9 pages).

Europe Supplementary Search Report dated Dec. 12, 2024 in related Application 22753369.2 filed Feb. 10, 2022 (11 pages).

* cited by examiner

METHODS AND DEVICES FOR AUGMENTING THE SPINE

CROSS-REFERENCE TO RELATED APPLICATIONS

N/A

TECHNICAL FIELD

This disclosure relates methods and devices for augmenting the spine.

BACKGROUND

As humans age they lose spinal muscularity and reduced function of stabilizing ligaments. Currently there are synthetic ligamentous systems that permit anchorage to the spinal column, but are designed to be fixed to a rod system or bone screws in order to obtain fusion or stabilize individual vertebral segments. Common posterior ligament approaches involve techniques and devices which require looping around a lamina or transverse process, or use of a bone screw such as a pedicle screw for fixation, or involve a connector system to fixate onto a bone screw or a metal rod. Anterior ligament systems are arriving on the market designed to couple bone screws to one-another and exert forces between vertebral bodies.

There is a desire for a technology to augment the posterior spine that does not require segmental fixation to bone via looping around bone structures (for example lamina or spinous process) or anchorage to the vertebral body via a bone screw for treatment of a medical condition. Such current approaches require significant soft tissue dissection and morbidity to the patient, as well as a loss of motion and flexibility. A less aggressive approach of augmenting natural ligaments and tendons is needed to provide dynamic stabilization to the spinal column over extended segments. However, this technology does not exist. Accordingly, this disclosure enables such technology.

SUMMARY

In one embodiment the present disclosure provides a ligament augmentation device or system positioned posteriorly to the vertebral bodies and muscular structures, and attached to natural soft tissues, spinous processes, or any component of a pre-existing spinal fixation device or system, not requiring deep dissection of muscle and ligament throughout its course. The present system is not designed with an intent to fuse all the augmented levels, which clearly distinguishes the present system from current uses of ligament systems. The present system generally employs a ligamentous line comprising natural ligaments (auto- or allo-graft), or synthetic ligaments, herein referred to as "ligamentous systems or devices." The attachment to spinal structures can occur via sutures, loops, staples or other anchoring devices designed for fixation to supraspinous ligaments, spinous processes, interspinous ligaments, fascia and muscle as well as any other surrounding soft tissues in proximity to the posterior aspects of spinal vertebrae, the sacrum or pelvic bones, or any pre-existing spinal fixation device or system.

The present disclosure provides a device to restrict interspinous motion across a plurality of segments of a spinal column in a patient, comprising at least a first ligamentous line attached to a spinous process, a soft tissue in proximity to posterior aspects of a spinal vertebrae, or a pre-existing spinal fixation device or system, wherein the device crosses a plurality of segments of the spinal column of the patient without segmental bone anchorage. In certain embodiments the device does not involve more than one bone screw on each side of the spine. In some embodiments the device is attached to the spinous process. In other embodiments a first end or a second end of the device is anchored to the spinous process. In further embodiments the device is anchored to the spinous process via a bone fixation device. In particular embodiments the bone fixation device is a bone screw.

In additional embodiments of the present disclosure the device is attached to the soft tissue in proximity to posterior aspects of a spinal vertebrae. In certain embodiments the device is attached to a tendon, a ligament, a cartilage, or a muscle. In particular embodiments the device is attached via sewing or binding. In some embodiments the device is attached to a pre-existing spinal fixation device or system, including, but not limited to, a pre-existing spinal bone screw. In such embodiments the pre-existing spinal bone screw can be located in a body of a vertebrae. In other embodiments the device is attached to a pre-existing spinal rod.

In certain embodiments the ligamentous line is biocompatible. In further embodiments the ligamentous line comprises a ligament autograft, a ligament allograft, or a synthetic material. In particular embodiments the synthetic material is a polymer, a membrane or a fiber. In some embodiments the synthetic material is expanded polytetrafluoroethylene, commonly known as GORE-TEX®, or poly-para-phenylene terephthalamide, commonly known as KEVLAR®. In yet other embodiments the ligamentous line is elastic. In various embodiments the ligamentous line stretches from a first side to a second side, or from a first top end to a second bottom end. In certain embodiments the ligamentous line has less elasticity at a first top end or a second bottom end than at a middle portion of the ligamentous line. In some embodiments the ligamentous line is woven or braided. In particular embodiments the elasticity of the ligamentous line is based on the weave or braiding of the ligamentous line. In additional embodiments the ligamentous line is flat, semi-circular, circular, ovoid, triangular, square, or rectangular, or any combination thereof.

In further embodiments of the present disclosure the ligamentous line is indirectly attached to the spinous process or soft tissue in proximity to posterior aspects of a spinal vertebrae. In some embodiments the device further comprises a casing surrounding the at least a first ligamentous line, and wherein the casing is attached to the spinous process or soft tissue in proximity to posterior aspects of a spinal vertebrae. In certain embodiments the casing is attached to the spinous process or soft tissue in proximity to posterior aspects of a spinal vertebrae with a compound, such as, but not limited to, a glue or a putty. In other embodiments the casing is a tube, a sleeve, a partial cylinder, or a trough surrounding the line, or any combination thereof. In various embodiments the casing has a cross section that is circular, oval, arcuate, V-shaped, U shaped, J-shaped, D-shaped, C-shaped, semicircular, curved, or flat, or any combination thereof.

In additional embodiments of the present disclosure the device further comprises an antibiotic, an analgesic, an anti-inflammatory, a steroid, or an anti scarring agent. In some embodiments the device further comprises at least a second ligamentous line. In certain embodiments the at least a first ligamentous line and the at least a second ligamentous line are comprised of different materials. In other embodiments the at least a first ligamentous line and the at least a second ligamentous line are arranged in parallel or overlap.

The present disclosure also provides a method of restricting interspinous motion across a plurality of segments of a spinal column in a patient, comprising attaching a device comprising at least a first ligamentous line attached to a spinous process, a soft tissue in proximity to posterior aspects of a spinal vertebrae, or a pre-existing spinal fixation device or system, wherein the device crosses a plurality of segments of the spinal column of the patient without segmental bone anchorage. In certain embodiments the device is inserted into the patient by a surgeon, a computer-assisted surgical device, a robotic surgical device, a minimally invasive procedure, or percutaneous placement.

Other objects and features of the present disclosure will be in part apparent and in part pointed out hereinafter.

DETAILED DESCRIPTION OF PREFERRED EMBODIMENTS

Figure 1:
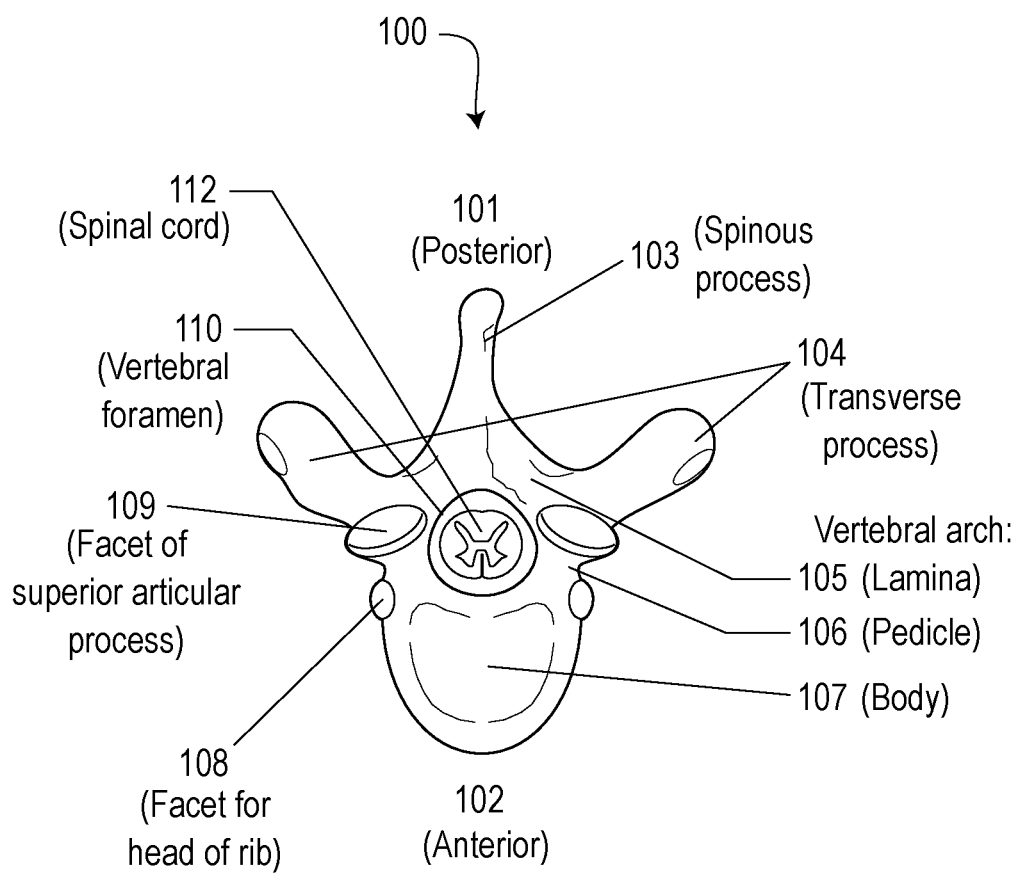
FIG. 1 shows a diagram of a posterior/anterior cross-section of a vertebrae, with various features of the vertebrae indicated.

Generally, this disclosure discloses a device for augmenting the spine comprising at least a first ligamentous line attached to either a spinous process, a soft tissue in proximity to posterior aspects of a spinal vertebrae, or a pre-existing spinal fixation device or system. The device generally crosses multiple segments of the spinal column of the patient without segmental bone anchorage, and generally does not involve more than one bone screw on each side of the spine. In certain embodiments of the present disclosure the ligamentous line(s) can be encased or overlaid by a protective member or casing, which can optionally be covered by a compound. In certain such embodiments the ligamentous line can be indirectly attached to either a spinous process, a soft tissue in proximity to posterior aspects of a spinal vertebrae, or a pre-existing spinal fixation device or system. The present disclosure thus also provides a method of diagnosing, monitoring, or treating a medical condition of the user, which can include extending the ligamentous line from an upper region of the spine to a lower region of the spine based on attaching the device to the upper region or the lower region. The presently disclosed method of treatment can generally include positioning a guide along the ligamentous line such that the guide guides the ligamentous line and thereby allows the ligamentous line to remain unimpeded and free moving between or relative to the upper region and the lower region of the spine, and/or in multiple dimensions. The ligamentous line can be encased in a sheath through or within which the ligamentous line can be moved in one or more dimensions or directions. The sheath can be coupled to a spinous process, a soft tissue in proximity to posterior aspects of a spinal vertebrae, or a pre-existing spinal fixation device or system using a compound. The compound can be shaped as a tunnel through which the ligamentous line extends. In some embodiments, the ligamentous line spans posteriorly between the desired upper region and lower region of the spine. In some embodiments, the ligamentous line may be positioned posteriorly to the spine. Note that this disclosure may be embodied in many different forms and should not be construed as necessarily being limited to various embodiments disclosed herein. Rather, these embodiments are provided so that this disclosure is thorough and complete, and fully conveys various concepts of this disclosure to skilled artisans.

In certain aspects of the present disclosure the spinal augmentation device or ligamentous line can also be used to deliver various drugs or other substances, or combinations of drugs or other substances, to the region of the spine being augmented. For example the spinal augmentation device or ligamentous line can be used to deliver an antibiotic, an analgesic, an anti-inflammatory, a steroid, an anti-scarring agent, a scarring agent, a hormone, a bone forming agent, an anti-resorptive agent, an angiogenesis factor, or a molecule to modify the local tissue healing and integration, or combinations thereof. In certain embodiments an antibiotic such as amoxicillin, penicillin, sulfa drugs, erythromycin, streptomycin, tetracycline, clarithromycin, terconazole, azithromycin, bacitracin, ciprofloxacin, evofloxacin, ofloxacin, levofloxacin, moxifloxacin, gatifloxacin, aminoglycosides, tobramycin, gentamicin, or a polymyxin B combination such as of polymyxin B/trimethoprim, polymyxin B/bacitracin, or polymyxin B/neomycin/gramicidin, or combinations thereof, an analgesic such as salicin, acetylsalicylic acid, sodium salicylate, acetaminophen, or bromelain or combinations thereof, a non-steroidal anti-inflammatory drug (NSAID) such as piroxicam, aspirin, salsalate, diflunisal, ibuprofen, ketoprofen, nabumetone, piroxicam, naproxen, diclofenac, indomethacin, sulindac, tolmetin, etodolac, ketorolac, oxaprozin, or celecoxib or combinations thereof, a steroid such as glucocorticoids, aprogestins, amineralocorticoids, corticosteroids, cortisone, hydrocortisone, prednisone, prednisolone, methylprednisone, triamcinolone, fluorometholone, dexamethasone, medrysone, betamethasone, loteprednol, fluocinolone, flumethasone, rimexolone mometasone, androgens, testosterone, methyltestosterone, or danazol or combinations thereof, an anti-scarring agent such as mitomycin-C, imiquimod, interferon, doxorubicin, verapamil, retinoic acid, tamoxifen, corticosteroids, bleomycin, silicone-based agents or 5-fluorouracil, or combinations thereof can be delivered by the ligamentous line and spinal augmentation devices as described herein. In certain embodiments the scarring agent can be used to promote adherence and/or integration of surrounding tissue. In certain embodiments the bone forming agents can include, but are not limited to, members of the fibroblast growth factor family, including acidic and basic fibroblast growth factor (FGF-1 and FGF-2) and FGF-4; members of the platelet-derived growth factor (PDGF) family, including PDGF-AB, PDGF-BB and PDGF-AA; EGFs; VEGF; members of the insulin-like growth factor (IGF) family, including IGF-I and -II; the TGF-.beta. superfamily, including TGF-.beta.1, 2 and 3; osteoid-inducing factor (OIF), angiogenin(s); endothelins; hepatocyte growth factor and keratinocyte growth factor; members of the bone morphogenetic proteins (BMPs) BMP-1, BMP-3, BMP-2, OP-1, BMP-2A, BMP-2B, BMP-7 and BMP-14, including MP-52; HBGF-1 and HBGF-2; growth differentiation factors (GDFs), members of the hedgehog family of proteins, including indian, sonic and desert hedgehog; ADMP-1; bone-forming members of the interleukin (IL) family; GDF-5; and members of the colony-stimulating factor (CSF) family, including CSF-1, G-CSF, and GM-CSF; and combinations or isoforms thereof. In certain embodiments the anti-resorptive agent can be a highly specific cytokine antagonist comprising infliximab, estrogen, selective estrogen receptor modulators (SERMs), biphosphonates, calcitonin, osteoprotegrin (OPG), agents that inhibit a cathepsin selected from the group consisting of cathepsin B, cathepsin L and cathepsin K, statins, alendronate, etidronate or risedronate, or combinations thereof. In certain embodiments, the molecule to modify the local tissue healing and integration can be angiogenesis factors including, but not limited to, vascular endothelial growth factor (VEGF) or vascular permeability factor (VPF), members of the fibroblast growth factor family, including acidic fibroblast growth factor (aFGF) and basic fibroblast growth factor (bFGF), interleukin-8 (IL-8), epidermal growth factor (EGF), platelet-derived growth factor (PDGF) or platelet-derived endothelial cell growth factor (PD-ECGF), transforming growth factors alpha and beta (TGF-α, TGF-β), tumor necrosis factor alpha (TNF-α), hepatocyte growth factor (HGF), granulocyte-macrophage colony stimulating factor (GM-CSF), insulin growth factor-1 (IGF-1), angiogenin, angiotropin, angiotensin, fibrin or nicotinamide, or combinations thereof In various aspects of the present disclosure, the spinal augmentation device or ligamentous line can be placed in position by a surgeon, a computer-assisted surgical device, a robotic surgical device, a minimally invasive procedure, or percutaneous placement. Examples of such placement devices and techniques include, but are not limited to, those described in U.S. Pat. Nos. 10,893,910, 10,864,057, 10,828, 116, 10,548,620, 10,463,404, 10,349,986, 10,292,778, 10,265,128, 10,201,391, 10,004,562, 9,788,966, 9,320,604 and 9,283,048, each of which is incorporated herein by reference in its entirety.

In certain embodiments, the spinal augmentation device or ligamentous line can be absorbable over time. Poly-α-hydroxy aliphatic esters are bioabsorbable polymers that are being used extensively as implantation products (e.g., orthopaedics, drug delivery, scaffolds and sutures). Polylactic acid (PLA), polyglycolic acid (PGA) and polydioxanone (PDO) are currently approved by the U.S. Food and Drug Agency (FDA) for human clinical uses. Under ideal conditions, a bioabsorbable polymer can encourage healing while the body slowly metabolizes it, thus eliminating need for a second surgery that may be required when a metal alloy is implanted. Polymeric drug delivery devices prevent drug degradation and may also provide management of drug release by varying drug-to-polymer ratio, molecular weight and composition of the polymer. In various aspects of the present disclosure the spinal augmentation device or ligamentous line can be made from an absorbable polymer such as polylactic acid or polylactide, polyglycolic acid or polyglycolide, poly(p-dioxanone), various poly(ether esters), poly(amino acids), copolymers and terpolymers of lactide, glycolide, p-dioxanone, trimethylene carbonate, ε-caprolactone, poly(ethylene diglycolate), poly(ethoxyethylene diglycolate), polyethylene glycol, polyhydroxyalkanoate, poly anhydride, polycaprolactone, poly-L-lactic acid, poly-D-L-lactic acid, or polyphosphate ester, or combinations thereof.

Note that various terminology used herein can imply direct or indirect, full or partial, temporary or permanent, action or inaction. For example, when an element is referred to as being "attached," "on," "connected," or "coupled" to another element, then the element can be directly attached, on, connected, or coupled to another element or intervening elements can be present, including indirect or direct variants. In contrast, when an element is referred to as being "directly attached," "directly connected" or "directly coupled" to another element, then there are no intervening elements present.

As used herein, various singular forms "a," "an" and "the" are intended to include various plural forms as well, unless specific context clearly indicates otherwise.

As used herein, various presence verbs "comprises," "includes" or "comprising," "including" when used in this specification, specify a presence of stated features, integers, steps, operations, elements, or components, but do not preclude the presence or addition of one or more other features, integers, steps, operations, elements, components, or groups thereof.

As used herein, a term "or" is intended to mean an inclusive "or" rather than an exclusive "or." That is, unless specified otherwise, or clear from context, "X employs A or B" is intended to mean any of a set of natural inclusive permutations. That is, if X employs A; X employs B; or X employs both A and B, then "X employs A or B" is satisfied under any of the foregoing instances.

As used herein, a term "or others," "combination", "combinatory," or "combinations thereof" refers to all permutations and combinations of listed items preceding that term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth.

Skilled artisans understand that typically there is no limit on number of items or terms in any combination, unless otherwise apparent from the context.

As used herein, unless otherwise defined, all terms (including technical and scientific terms) used herein have the same meaning as commonly understood by one of ordinary skill in an art to which this disclosure belongs. Various terms, such as those defined in commonly used dictionaries, should be interpreted as having a meaning that is consistent with a meaning in a context of a relevant art and should not be interpreted in an idealized or overly formal sense unless expressly so defined herein.

As used herein, relative terms such as "below," "lower," "above," and "upper" can be used herein to describe one element's relationship to another element as illustrated in the set of accompanying illustrative drawings. Such relative terms are intended to encompass different orientations of illustrated technologies in addition to an orientation depicted in the set of accompanying illustrative drawings. For example, if a device in the set of accompanying illustrative drawings were turned over, then various elements described as being on a "lower" side of other elements would then be oriented on "upper" sides of other elements. Similarly, if a device in one of illustrative figures were turned over, then various elements described as "below" or "beneath" other elements would then be oriented "above" other elements. Therefore, various example terms "below" and "lower" can encompass both an orientation of above and below.

As used herein, a term "about" or "substantially" refers to a +/−10% variation from a nominal value/term. Such variation is always included in any given value/term provided herein, whether or not such variation is specifically referred thereto.

FIG. 1 shows a diagram of a posterior/anterior cross section of a vertebrae. In particular, as shown in FIG. 1, a vertebrae 100 of a user (e.g., a mammal, an animal, a human) includes a posterior portion 101, an anterior portion 102, a spinous process 103, transverse processes 104, lamina 105, pedicle 106, body 107, facet for the head of a rib 108, facet of superior articular process 109, and vertebral foramen 110, containing the spinal cord 112. Note that the device of the present disclosure can be applied to any vertebrae 100 of the spine.

Figure 2:
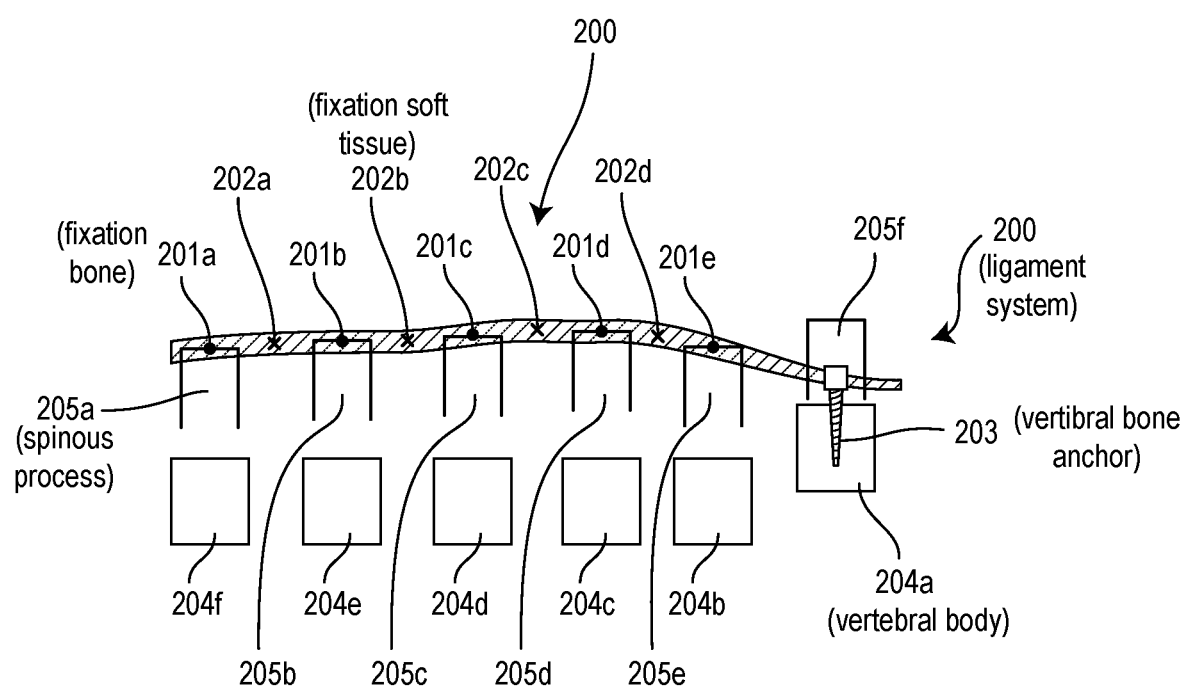
FIG. 2 shows a diagram of an embodiment of a device of the present disclosure, with one end of the device attached to a pre-existing vertebral bone anchor located in the vertebral body for installation onto a spinal structure in accordance with this disclosure.

FIG. 2 shows a device 200 (also in certain aspects referred to as a ligament system) in accordance with one or more embodiments of the present disclosure. Device 200 is attached to a pre-existing vertebral bone anchor 203 located in a vertebral body 204a. Although not shown, device 200 can alternatively be attached to any pre-existing bone fixation device (e.g., a hook, a rod, a screw, a wire, an anchor, a dart, or a loop) that is coupled (e.g., fastened, mated, interlocked, adhered, stapled, or tied) to a vertebrae (e.g., a transverse process, spinous process, lamina, or pars). As shown in FIG. 2, device 200 spans vertebral bodies 204b, 204c, 204d, 204e and 204f, and spinous process 205a, 205b, 205c, 205d, 205e and 205f. As shown in FIG. 2, device 200 is fixated 201a to bone of the spinous process 205a, fixated 201b to bone of the spinous process 205b, fixated 201c to bone of the spinous process 205c, and fixated 201d to bone of the spinous process 205d. Device 200 is also shown fixated to soft tissue 202a proximal to spinous process 205a, fixated to soft tissue 202b proximal to spinous process 205a, fixated to soft tissue 202c proximal to spinous process 205c, fixated to soft tissue 202d proximal to spinous process 205d, and fixated to soft tissue 202e proximal to spinous process 205e. However, note that the device 200 can be fixated to a tissue (e.g., hard or soft) or an implant (inserted or pre-existing) in proximity (e.g., about 1 inch or less) to the vertebrae. The device can be used to diagnose, monitor, or treat a medical condition. For example, the medical condition can include age related deformity of the spine, scoliosis, kyphosis, flatback, spondylosis, neurodegenerative deformity, trauma related instability or deformity, muscular degeneration, metabolic muscular or bone related pathologies, congenital or idiopathic conditions, iatrogenic pathology, infectious or post-infectious pathology.

Not shown in FIG. 2, a protective member (e.g., a tube, a sleeve, a partial cylinder, a trough) can encase all or a portion of the device and ligamentous line. The protective member can include synthetic material, organic material, metal, plastic, rubber, fabric, or silicon. The protective member can be coupled (e.g., fastened, mated, interlocked, adhered, stapled, tied) to soft tissue, spinous process or a pre-existing anchor. In various embodiments the protective member can have a cross section that is open-shaped, close-shaped, symmetrical, or asymmetrical (e.g., circular, oval, triangular, pentagonal, octagonal, arcuate, V-shaped, U-shaped, J-shaped, D-shaped, C-shaped, semicircular, curved, flat). In certain embodiments the protective member can be solid, semi solid, permeable, or semi-permeable. In additional embodiments the protective member can be rigid, semi-rigid, flexible, elastic, or resilient.

The device 200 comprises a ligamentous line (e.g., a transplanted ligament, or a synthetic material such as a tether, a cable, a chain, a wire, a rope, a belt, a band, a braid, a tube, or a cylinder) that extends (e.g., spans one or more vertebrae) from the anchor 203. The ligamentous line can be movable or displaceable (e.g., longitudinally, laterally, slideably, suspended) along the protected vertebrae. The terms "move," "movable," and "movement" include the common meaning of such terms, as well as displace, bend, flex, rotate, shift, displaceable, flexible, rotatable, shiftable, displacement, flexion, rotation, shifting, and includes any or all directions and dimensions. The ligamentous line can include metal, plastic, rubber, fabric, or silicon, or an autograft or an allograft. The ligamentous line can be flat, cylindrical, synthetic, elastic, rigid, woven, or braided. In certain embodiments the ligamentous line extends within the protective member. In alternative embodiments a compound (e.g., an adhesive, a putty, a glue, a bone cement) can be positioned over the protective member and a vertebrae surface (e.g., as an arcuate tunnel, a U-shaped tunnel, a C-shaped tunnel, a D-shaped tunnel, an O-shaped tunnel) such that the protective member is coupled (e.g., adhering, bonded) to a spinous process or a soft tissue in proximity to a spinal process.

The ligamentous line and, if present, the protective member can extend along a vertical plane (e.g., along the sagittal plane) and span from one or more fixation point across one or more vertebrae. In this scenario, the ligamentous line or the protective member do not cross the sagittal plane of the user. Alternatively the ligamentous line or the protective member can extend along a diagonal plane and span from one or more fixation point across one or more vertebrae. In this scenario, the ligamentous line or protective member do cross the sagittal plane of the user. In other embodiments the ligamentous line or the protective member can extend along a vertical plane (e.g., along the sagittal plane) and span from one or more fixation point across one or more vertebrae. In this scenario, the ligamentous line or the protective member do not cross the sagittal plane of the user. The ligamentous line or the protective member can contact or avoid contact with a vertebrae. The ligamentous line or the protective member can couple (e.g., fastening, mating, interlocking, adhering, stapling, tying) or avoid coupling to a vertebrae. Additionally, the ligamentous line or the protective member can extend along a horizontal plane (e.g., along a transverse plane of the user) and span from one or more fixation point across a vertebrae. In this scenario, the ligamentous line or the protective member are positioned on a common vertebrae and the ligamentous line or the protective member cross the sagittal plane of the user.

Figure 3:
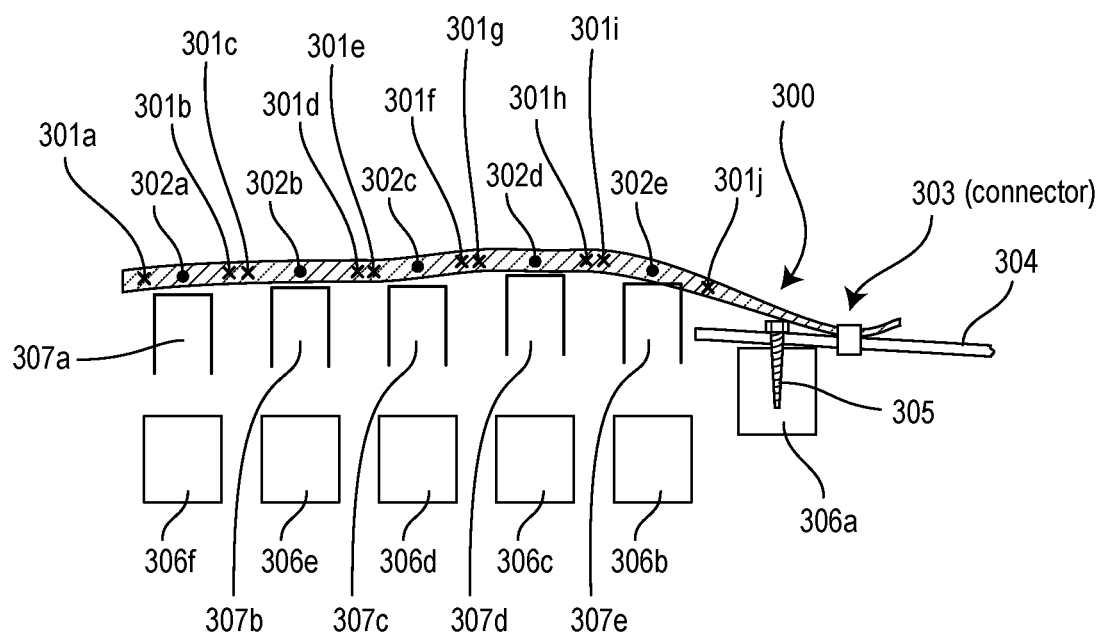
FIG. 3 shows a diagram of an embodiment of a device of the present disclosure, with one end of the device attached to a pre-existing rod attached to a vertebral bone anchor located in the vertebral body for installation onto a spinal structure in accordance with this disclosure.

FIG. 3 shows a device 300 (also in certain aspects referred to as a ligament system) in accordance with one or more embodiments of the present disclosure. Device 300 is attached via connector 303 to a pre-existing rod 304 attached to a pre-existing vertebral bone anchor 306 located in a vertebral body 306a. Although not shown, device 300 can alternatively be attached to any pre-existing bone fixation device (e.g., a hook, a rod, a screw, a wire, an anchor, a dart, or a loop) that is coupled (e.g., fastened, mated, interlocked, adhered, stapled, or tied) to a vertebrae (e.g., a transverse process, spinous process, lamina, or pars). As shown in FIG. 3, device 300 spans vertebral bodies 306a, 306b, 306c, 306d, 306e and 306f, and spinous process 307a, 307b, 307c, 307d, 307e and 307f. As shown in FIG. 3, device 300 is fixated 302a to bone of the spinous process 307a, fixated 302b to bone of the spinous process 307b, fixated 302c to bone of the spinous process 307c, fixated 302d to bone of the spinous process 307d, and fixated 302e to bone of the spinous process 307e. Device 300 is also shown fixated to soft tissue 301a and 302b proximal to spinous process 307a, fixated to soft tissue 301c and 301d proximal to spinous process 307b, fixated to soft tissue 301e and 301f proximal to spinous process 307c, fixated to soft tissue 301g and 301h proximal to spinous process 307d, and fixated to soft tissue 301i and 301j proximal to spinous process 307e.

Figure 4:
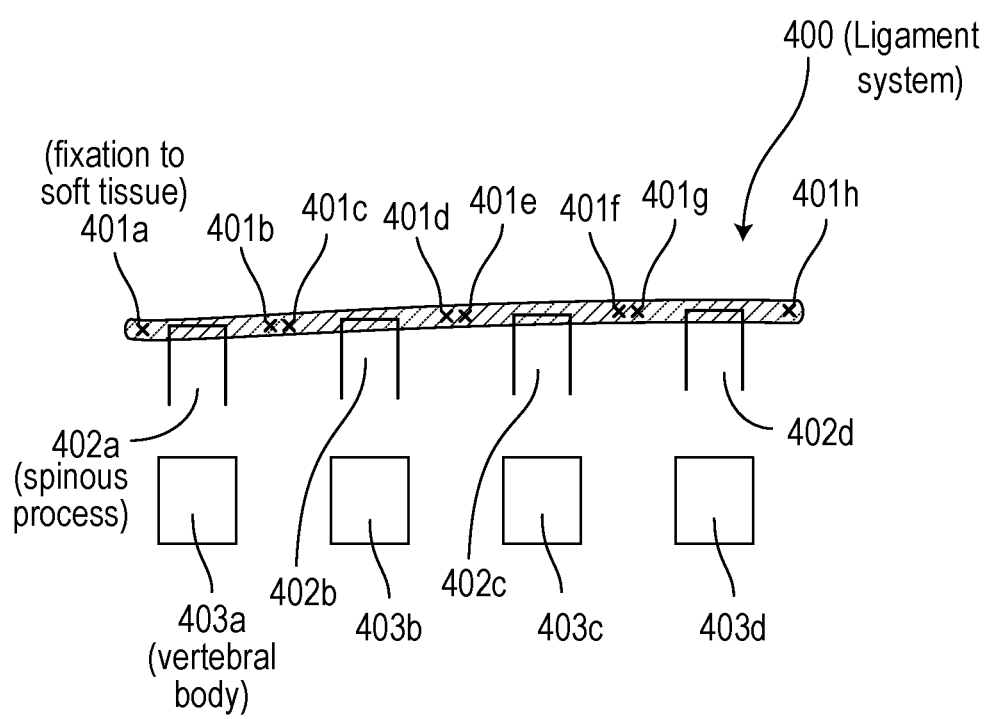
FIG. 4 shows a diagram of an embodiment of a device of the present disclosure attached to soft tissue proximal to several spinal processes, in accordance with this disclosure.

FIG. 4 shows a device 400 (also in certain aspects referred to as a ligament system) in accordance with one embodiment of the present disclosure. Device 400 spans spinous process 402a, 402b, 402c and 402d and vertebral bodies 403a, 403b, 403c and 403d. As shown in FIG. 4, device 400 is fixated to soft tissue at points 401a, 401b, 401c, 401d, 401e, 401f, 401g and 401h proximal to spinous process 402a, 402b, 402c and 402d.

Figure 5:
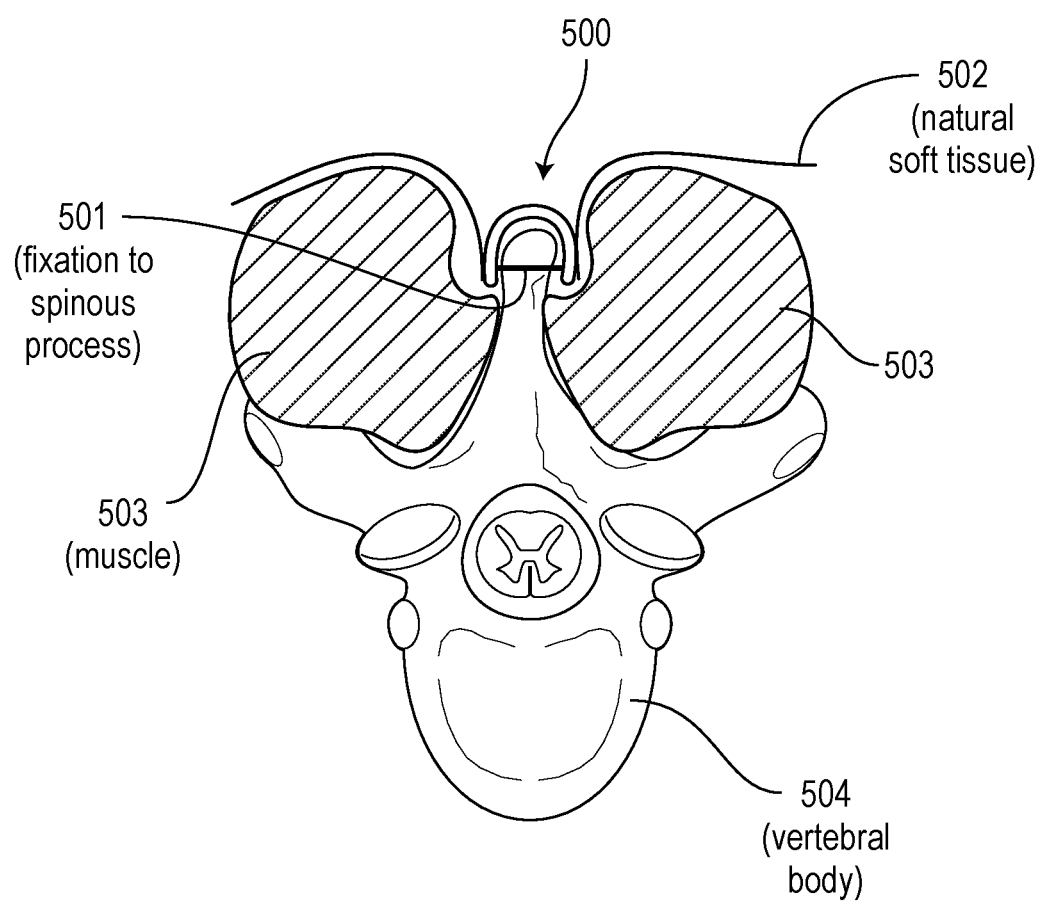
FIG. 5 shows a diagram of an embodiment of a device of the present disclosure attached to a spinal process proximal to natural soft tissue present near the muscles running along the vertebrae, in accordance with this disclosure.

FIG. 5 shows a diagram of a cross-section of a vertebrae with an embodiment of a device 500 (also in certain aspects referred to as a ligament system) comprising a ligamentous line in accordance with this disclosure. FIG. 5 shows fixation of the device 500 to spinous process 501, proximal to natural soft tissue 502 and muscle 503.

Figure 6:
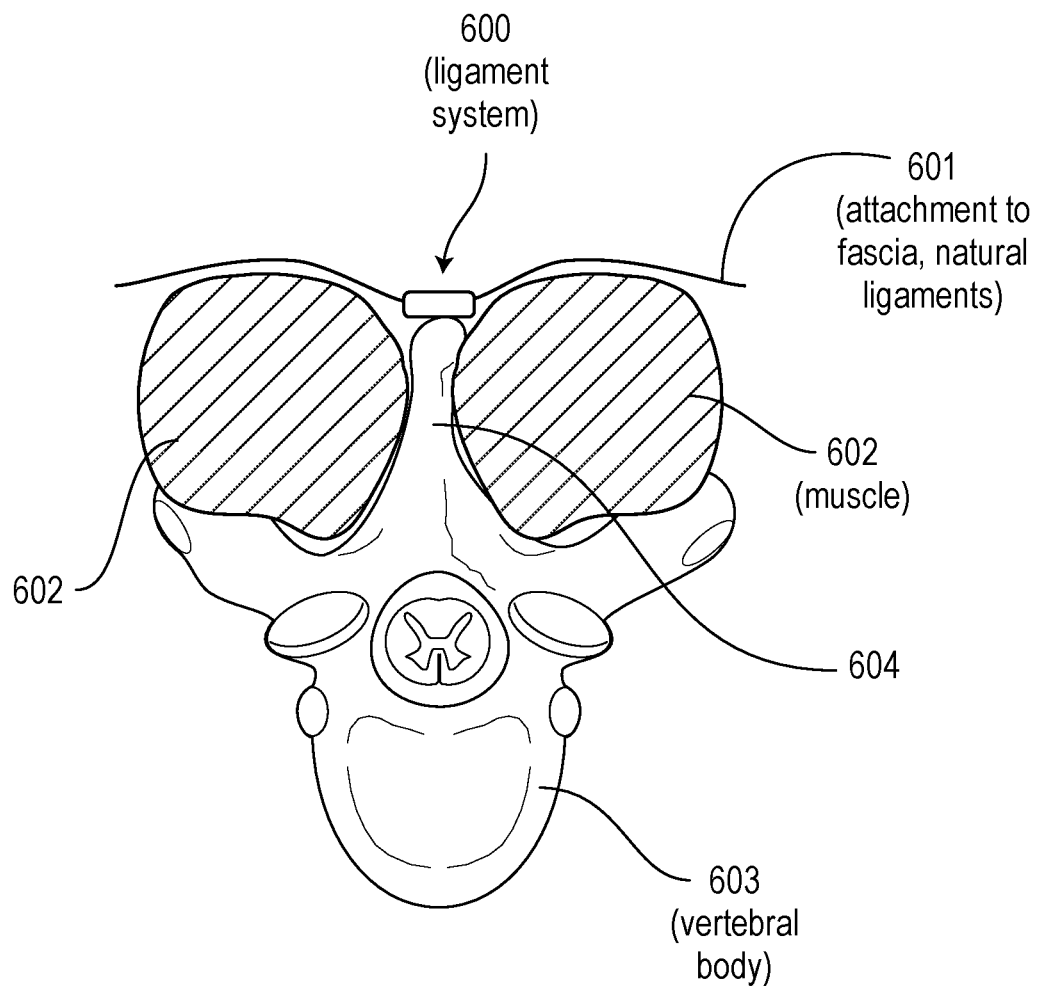
FIG. 6 shows a diagram of an embodiment of a device of the present disclosure attached to fasciae and dorsal to the natural ligaments, proximal to the muscles running along the vertebrae, in accordance with this disclosure.

FIG. 6 shows a diagram of a cross-section of a vertebrae with an embodiment of a device 600 (also in certain aspects referred to as a ligament system) comprising a ligamentous line in accordance with this disclosure. FIG. 6 shows fixation of the device 600 to fascia or natural ligaments 601, proximal to muscle 602 and spinous process 604. Also shown in FIG. 6 is vertebral body 603.

Figure 7:
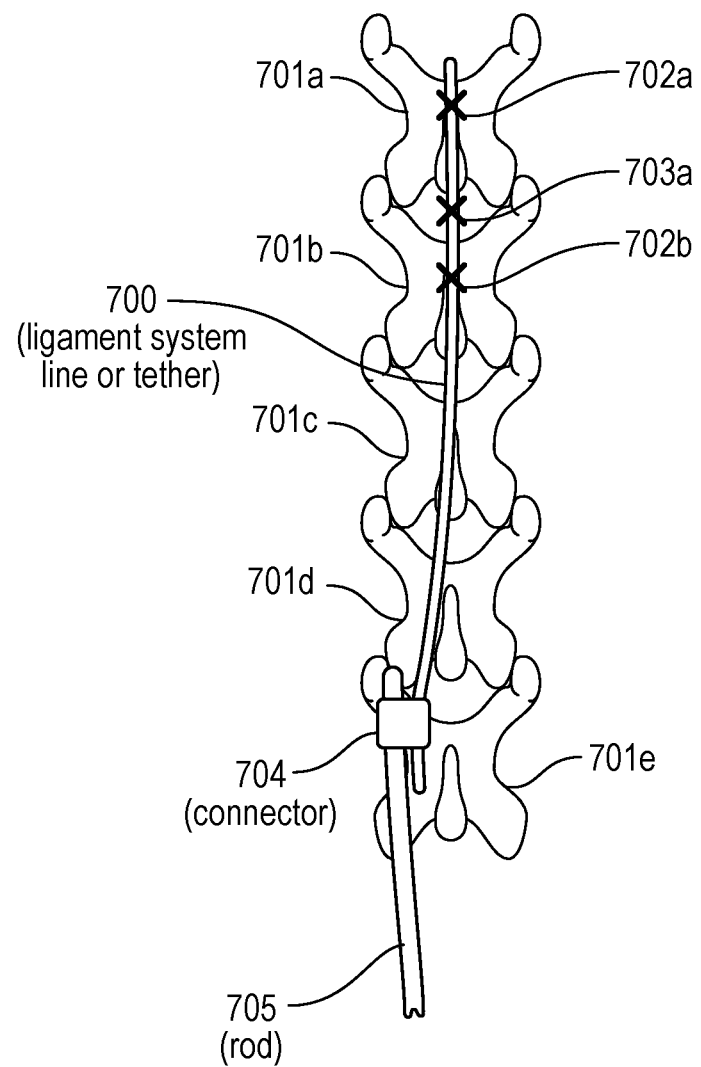
FIG. 7 shows a diagram of an embodiment of a device of the present disclosure attached on the first end to a spinous process and attached on the second end to a rod of a pre-existing spinal fixation device, the device also attached to a soft tissue or a non-bone tissue, such as cartilage, ligament or fasciae, between the first end and the second end, in accordance with this disclosure.

FIG. 7 shows a diagram of a cross-section of five vertebrae with an embodiment of a device 700 (also in certain aspects referred to as a ligament system) comprising a ligamentous line in accordance with this disclosure. FIG. 7 shows fixation of the device 700 via connector 704 to pre-existing rod 705 proximal to vertebrae 701e. As shown in FIG. 7, device 700 spans vertebrae 701a, 701b, 701c, 701d and 701e. As shown in FIG. 7, device 700 is fixated 702a to bone of the spinous process of vertebrae 701a, and fixated 702b to bone of the spinous process of vertebrae 701b. Device 700 is also shown fixated to soft tissue 703a proximal to spinous process of vertebrae 701a and 701b.

Figure 8:
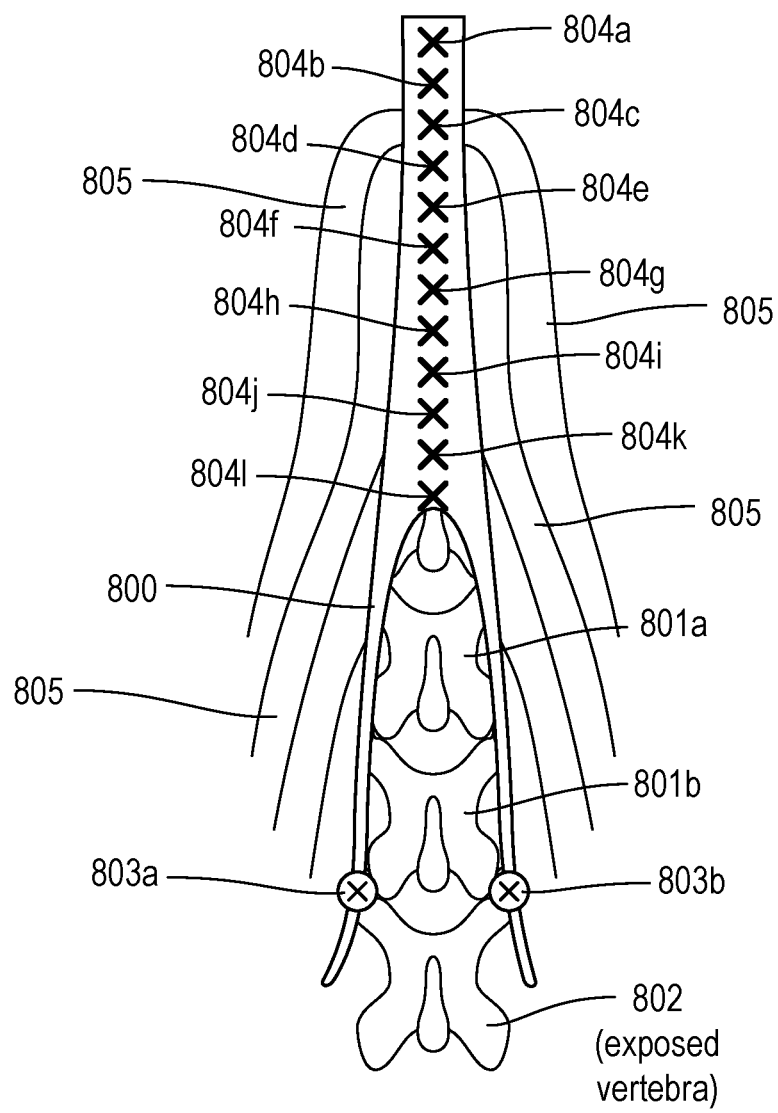
FIG. 8 shows a diagram of an embodiment of a device of the present disclosure attached at both ends to a pre-existing bone anchor and attached to a soft tissue or fasciae overlying or covering the vertebrae between the ends of the device, with one portion of the device located on one side of the spinal column and the other portion of the device located on the opposite side of the spinal column, in accordance with this disclosure.

FIG. 8 shows a diagram of a cross-section of three vertebrae (two partially exposed (801a and 801b) and one exposed (802)) with an embodiment of a device 800 (also in certain aspects referred to as a ligament system) comprising a ligamentous line in accordance with this disclosure. FIG. 8 shows fixation of the device 800 to pre-existing vertebral bone anchors 803a and 803b located in a vertebrae 802. As shown in FIG. 8, device 800 spans partially exposed vertebrae 801b and 801a, as well as a number of non-exposed vertebrae (not visible in FIG. 8). As shown in FIG. 8, device 800 is fixated 804a, 804b, 804c, 804d, 804e, 804f, 804g, 804h, 804i, 804j, 804k and 804l to soft tissue proximal to the non-exposed vertebrae (not visible in FIG. 8).

Figure 9:
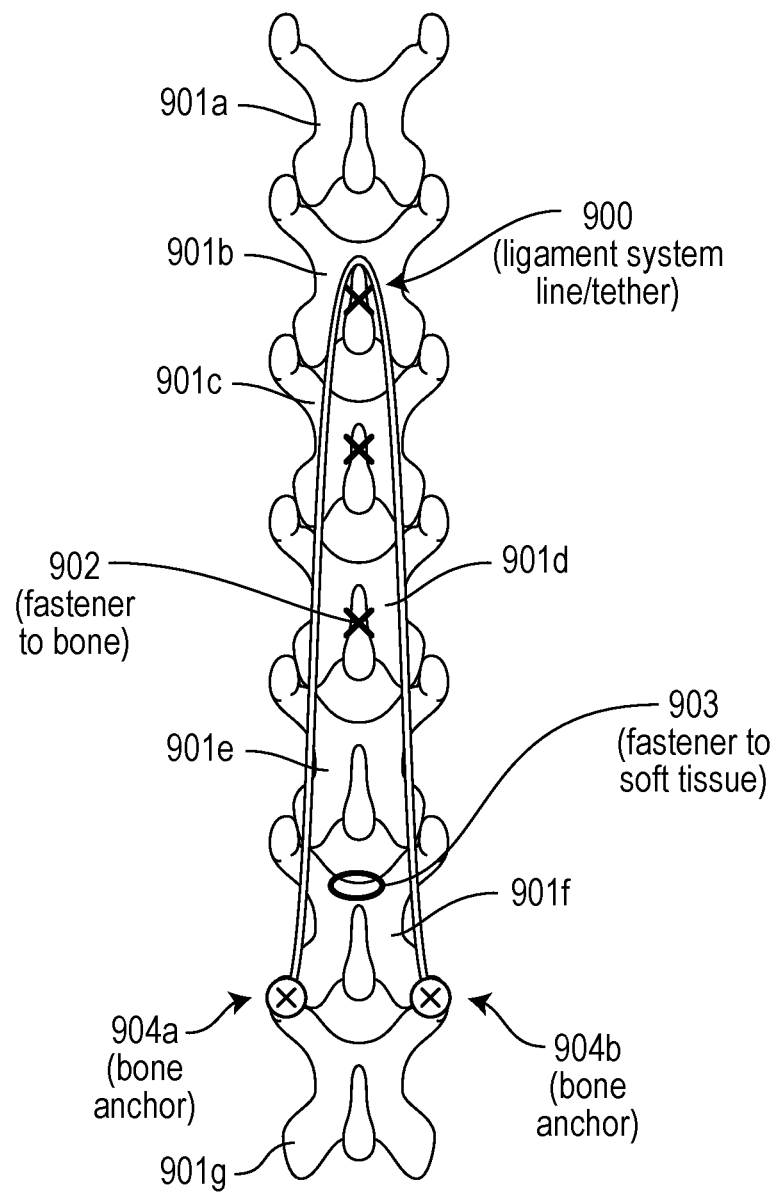
FIG. 9 shows a diagram of an embodiment of a device of the present disclosure attached at both ends to a pre-existing bone anchor, with one portion of the device attached to bone located on one side of the spinal column and the other portion of the device attached to soft tissue located on the opposite side of the spinal column, in accordance with this disclosure.

FIG. 9 shows a diagram of a cross-section of seven vertebrae with an embodiment of a device 900 (also in certain aspects referred to as a ligament system) comprising a ligamentous line in accordance with this disclosure. FIG. 9 shows fixation of the device 900 to pre-existing vertebral bone anchors 904a and 904b located in a vertebrae 901g. As shown in FIG. 9, device 900 spans vertebrae 901a, 901b, 901c, 901d, 901e, and 901f. As shown in FIG. 9, device 900 is fixated 902 to bone of the spinous process of vertebrae 901d, and fixated to soft tissue 903 proximal to spinous process of vertebrae 901f.

Note that all of such forms of fixation can be mixed and matched in any permutational combinatory manner, as disclosed herein. For example, the ligamentous line or the protective member can be attached via one of such methods, at least two of such methods, at least three of such methods, or more or none of any one of such points within a human body. Features described with respect to certain embodiments may be combined in or with various some embodiments in any permutational or combinatory manner. Different aspects or elements of example embodiments, as disclosed herein, may be combined in a similar manner.

Although the terms first, second, can be used herein to describe various elements, components, regions, layers, or sections, these elements, components, regions, layers, or sections should not necessarily be limited by such terms. These terms are used to distinguish one element, component, region, layer or section from another element, component, region, layer or section. Thus, a first element, component, region, layer, or section discussed below could be termed a second element, component, region, layer, or section without departing from various teachings of this disclosure.

Features described with respect to certain example embodiments can be combined and sub-combined in or with various other example embodiments. Also, different aspects or elements of example embodiments, as disclosed herein, can be combined and sub-combined in a similar manner as well. Further, some example embodiments, whether individually or collectively, can be components of a larger system, wherein other procedures can take precedence over or otherwise modify their application. Additionally, a number of steps can be required before, after, or concurrently with example embodiments, as disclosed herein. Note that any or all methods or processes, at least as disclosed herein, can be at least partially performed via at least one entity in any manner.

Example embodiments of this disclosure are described herein with reference to illustrations of idealized embodiments (and intermediate structures) of this disclosure. As such, variations from various illustrated shapes as a result, for example, of manufacturing techniques or tolerances, are to be expected. Thus, various example embodiments of this disclosure should not be construed as necessarily limited to various particular shapes of regions illustrated herein, but are to include deviations in shapes that result, for example, from manufacturing.

Any or all elements, as disclosed herein, can be formed from a same, structurally continuous piece, such as being unitary, or be separately manufactured or connected, such as being an assembly or modules. Any or all elements, as disclosed herein, can be manufactured via any manufacturing processes, whether additive manufacturing, subtractive manufacturing, or other any other types of manufacturing. For example, some manufacturing processes include three dimensional (3D) printing, laser cutting, computer numerical control routing, milling, pressing, stamping, vacuum forming, hydroforming, injection molding, lithography, and so forth.

Various corresponding structures, materials, acts, and equivalents of all means or step plus function elements in various claims below are intended to include any structure, material, or act for performing the function in combination with other claimed elements as specifically claimed. Various embodiments were chosen and described in order to best explain various principles of this disclosure and various practical applications thereof, and to enable others of ordinary skill in a pertinent art to understand this disclosure for various embodiments with various modifications as are suited to a particular use contemplated.

This detailed description has been presented for various purposes of illustration and description, but is not intended to be fully exhaustive or limited to this disclosure in various forms disclosed. Many modifications and variations in techniques and structures will be apparent to those of ordinary skill in an art without departing from a scope and spirit of this disclosure as set forth in various claims that follow. Accordingly, such modifications and variations are contemplated as being a part of this disclosure. A scope of this disclosure is defined by various claims, which include known equivalents and unforeseeable equivalents at a time of filing of this disclosure.

The invention claimed is:

1. A device, comprising:
   at least a first ligamentous line having a first end and a second end, wherein a first portion of the at least the first ligamentous line at or at about the first end is configured for direct coupling to a first portion of soft tissue in proximity to posterior aspects of a first spinal vertebrae, wherein a second portion of the at least the first ligamentous line at or at about the second end is configured for coupling to at least one of a second portion of soft tissue on a first side of the spine in proximity to posterior aspects of a second spinal vertebrae, or a first bone anchor, and wherein a third portion of the at least the first ligamentous line at or at about the second end is configured for coupling to at least one of a third portion of soft tissue on a second side of the spine in proximity to posterior aspects of the second spinal vertebrae, or a second bone anchor, wherein the at least the first ligamentous line between the first portion and the second portion is of a length sufficient to cross a plurality of segments of a spinal column of a patient without segmental bone anchorage, and wherein the at least the first ligamentous line is configured to restrict interspinous motion across a plurality of segments of the spinal column of the patient.

2. The device of claim 1, wherein the device is configured to not require more than one bone screw on each side of the spine.

3. The device of claim 1, wherein the second end is configured for coupling to a first spinous process.

4. The device of claim 3, wherein the second portion is configured for coupling to the first spinous process or the third portion is configured for coupling to a second spinous process.

5. The device of claim 1, wherein the first portion of the at least the first ligamentous line is configured for coupling to the first portion of soft tissue.

6. The device of claim 5, wherein the soft tissue comprises a tendon, a ligament, a cartilage, or a muscle.

7. The device of claim 1, wherein the first portion of the at least the first ligamentous line or second portion of the at least the first ligamentous line is configured for coupling via sewing or binding.

8. The device of claim 1, wherein the ligamentous line is biocompatible.

9. The device of claim 8, wherein the ligamentous line comprises a ligament autograft, a ligament allograft, or a synthetic material.

10. The device of claim 9, wherein the at least the first ligamentous line is woven or braided.

11. The device of claim 10, wherein the elasticity of the at least the first ligamentous line is based on the weave or braiding of the at least the first ligamentous line.

12. The device of claim 8, wherein the ligamentous line comprises a synthetic material, and wherein the synthetic material is a polymer, a membrane or a fiber.

13. The device of claim 8, wherein the ligamentous line comprises a synthetic material, and wherein the synthetic material is a material comprising expanded polytetrafluoroethylene or poly-para-phenylene terephthalamide.

14. The device of claim 1, wherein the at least the first ligamentous line is elastic.

15. The device of claim 14, wherein the at least the first ligamentous line is configured for stretching from a first side of the spinal column in the patient to a second side of the spinal column in the patient, or from the first end to the second end.

16. The device of claim 14, wherein the at least the first ligamentous line has less elasticity at the first end or the second end than at a middle portion of the at least the first ligamentous line.

17. The device of claim 1, wherein the at least the first ligamentous line is flat, semi-circular, circular, ovoid, triangular, square, or rectangular, or any combination thereof.

18. The device of claim 1, wherein the coupling of the second portion is indirect.

19. The device of claim 18, wherein the device further comprises a casing surrounding the at least the first ligamentous line, and wherein the coupling is via the casing.

20. The device of claim 19, wherein the casing is coupled via a compound.

21. The device of claim 20, wherein the compound is a glue or a putty.

22. The device of claim 19, wherein the casing is a tube, a sleeve, a partial cylinder, or a trough surrounding the line, or any combination thereof.

23. The device of claim 19, wherein the casing has a cross section that is circular, oval, arcuate, V-shaped, U-shaped, J-shaped, D-shaped, C-shaped, semicircular, curved, or flat, or any combination thereof.

24. The device of claim 1, wherein the device further comprises an antibiotic, an analgesic, an anti-inflammatory, a steroid, or an anti-scarring agent.

25. The device of claim 1, further comprising at least a second ligamentous line.

26. The device of claim 25, wherein the at least the first ligamentous line and the at least the second ligamentous line are comprised of different materials.

27. The device of claim 25, wherein the at least the first ligamentous line and the at least the second ligamentous line are arranged in parallel or overlap.

28. A method, comprising
directly coupling a first portion of a ligamentous line at or at about a first end of the ligamentous line to a first portion of soft tissue in proximity to posterior aspects of a first spinal vertebrae;
directly coupling a second portion of the ligamentous line at or at about a second end of the ligamentous line to a second portion of soft tissue on a first side of the spine in proximity to posterior aspects of a second spinal vertebrae or a first bone anchor associated with the second spinal vertebrae,
directly coupling a third portion of the ligamentous line at or at about the second end of the ligamentous line to a third portion of soft tissue on a second side of the spine in proximity to posterior aspects of the second spinal vertebrae or a second bone anchor; and
positioning the ligamentous line across a plurality of segments of the spinal column of the patient without segmental bone anchorage thereby restricting interspinous motion across the plurality of segments of the spinal column in the patient.

29. The method of claim 28, further comprising inserting the ligamentous line into a patient by a surgeon, a computer-assisted surgical device, a robotic surgical device, a minimally invasive procedure, or percutaneous placement.

30. A device, comprising:
at least a first ligamentous line having a first end and a second end, wherein a first portion of the at least the first ligamentous line at or at about the first end is configured for coupling directly to at least one first portion of soft tissue in proximity to posterior aspects of a first spinal vertebrae, wherein a second portion of the at least the first ligamentous line at or at about the second end is configured for coupling directly to a second portion of soft tissue on a first side of the spine in proximity to posterior aspects of a second spinal vertebrae or a first bone anchor, wherein a third portion of the at least the first ligamentous line at or at about the second end is configured for coupling directly to a third portion of soft tissue on a second side of the spine in proximity to posterior aspects of the second spinal vertebrae or a second bone anchor, wherein the at least the first ligamentous line between the first portion and the second portion is of a length sufficient to cross a plurality of segments of a spinal column of a patient without segmental bone anchorage, and wherein the at least the first ligamentous line is configured to restrict interspinous motion across a plurality of segments of the spinal column of the patient.

31. A device, comprising:
at least a first ligamentous line having a first end portion, a second end portion, and a third end portion wherein the first end portion of the at least the first ligamentous line is configured for coupling directly to at least one first portion of soft tissue in proximity to posterior aspects of a first spinal vertebrae, wherein the second end portion of the at least the first ligamentous line is configured for coupling directly to a second portion of soft tissue or a first bone anchor on a first side of the spine in proximity to posterior aspects of a second spinal vertebrae, wherein the third end portion of the at least the first ligamentous line is configured for coupling directly to a third portion of soft tissue or a second bone anchor on a second side of the spine in proximity to posterior aspects of the second spinal vertebrae, wherein the at least the first ligamentous line between the first portion and the second portion is of a length sufficient to cross a plurality of segments of a spinal column of a patient without segmental bone anchorage, and wherein the at least the first ligamentous line is configured to restrict interspinous motion across a plurality of segments of the spinal column of the patient.

32. A device, comprising:
at least a first ligamentous line having a first end and a second end, wherein a first portion of the at least the first ligamentous line at or at about the first end is configured for direct coupling to a first portion of soft tissue in proximity to posterior aspects of a first spinal vertebrae, wherein a second portion of the at least the first ligamentous line at or at about the second end is configured for coupling to a first pre-existing spinal fixation device or system, and wherein a third portion of the at least the first ligamentous line at or at about the second end is configured for coupling to a second pre-existing spinal fixation device or system, wherein the at least the first ligamentous line between the first portion and the second portion is of a length sufficient to cross a plurality of segments of a spinal column of a patient without segmental bone anchorage, and wherein the at least the first ligamentous line is configured to restrict interspinous motion across a plurality of segments of the spinal column of the patient.

33. The device of claim 32, wherein the coupling is via a pre-existing spinal rod.

34. A device, comprising:
at least a first ligamentous line having a first end portion, a second end portion, and a middle portion, wherein the middle portion of the at least the first ligamentous line is configured for coupling directly to at least one first portion of soft tissue in proximity to a spinous process of a first spinal vertebrae, wherein the first end portion of the at least the first ligamentous line is configured for coupling directly to at least one of a second portion of soft tissue or a first bone anchor on a first side of the spine in proximity to posterior aspects of a second spinal vertebrae, wherein the second end portion of the at least the first ligamentous line is configured for coupling directly to at least one of a third portion of soft tissue or a second bone anchor on a second side of the spine in proximity to posterior aspects of the second spinal vertebrae, wherein the at least the first ligamentous line between the first portion and the second portion is of a length sufficient to cross a plurality of segments of a spinal column of a patient without segmental bone anchorage, and wherein the at least the first ligamentous line is configured to restrict interspinous motion across a plurality of segments of the spinal column of the patient.

* * * * *